(12) United States Patent
Silvian

(10) Patent No.: US 6,477,414 B1
(45) Date of Patent: Nov. 5, 2002

(54) TRANSFORMER ASSEMBLY FOR IMPLANTABLE CARDIAC STIMULATION DEVICE

(75) Inventor: Sergiu Silvian, La Crescenta, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/844,035

(22) Filed: Apr. 26, 2001

(51) Int. Cl.$^7$ ................................................. A61N 1/39

(52) U.S. Cl. .......................................................... 607/5

(58) Field of Search ........................................ 607/4–9

(56) References Cited

U.S. PATENT DOCUMENTS 5,466,254 A   11/1995  Helland ...................... 607/123
5,814,082 A  *  9/1998  Fayram et al.

* cited by examiner

Primary Examiner—Scott M. Getzow

(57) ABSTRACT

The transformer assembly is coupled between a power supply and a pulse delivery circuit of the implantable cardiac stimulation device for charging a pair of defibrillation capacitors for delivering defibrillation pulses. The power transformer assembly is formed from a printed circuit board (PCB) having a set of transformer coil turns embedded therein and a transformer core mounted adjacent to the windings of the PCB. By embedding the coil of the transformer within the PCB, the transformer may be more easily integrated with other components of the stimulation device so that the overall size of the stimulation device may be reduced. Moreover, the use of a PCB helps avoid reliability problems that might otherwise occur in the fabrication, assembly and operation of the device. In one specific configuration described herein, the transformer assembly includes a primary and two secondary transformers. The primary transformer is used as a flyback transformer for charging the pair of defibrillation capacitors. The two secondary transformers are used to provide voltage for selectively switching on a set of transistors formed in an H-bridge configuration so as to apply charge stored in the capacitors in biphasic pulse waveform to the heart. The coils of the primary and secondary transformers are all embedded within a single PCB. In another configuration, only the coil of the primary transformer is embedded within the PCB. The coils of the two secondary transformers are affixed to the surface of the PCB.

14 Claims, 6 Drawing Sheets

TRANSFORMER ASSEMBLY FOR IMPLANTABLE CARDIAC STIMULATION DEVICE

FIELD OF THE INVENTION

The invention generally relates to implantable cardiac stimulation devices such as implantable cardioverter defibrillators (ICDS) and in particular to power transformers for use within implantable cardiac stimulation devices.

BACKGROUND OF THE INVENTION

An ICD is a type of implantable cardiac stimulation device which recognizes atrial fibrillation or ventricular fibrillation in the heart of a patient and delivers electrical shocks to terminate the fibrillation. Typically, defibrillation shocks are delivered by a pulse delivery circuit connected to a pair of capacitors charged at a combined voltage of about 1500 volts. In response to the detection of fibrillation, the pulse delivery circuit discharges the capacitors to provide a defibrillation pulse having a desired shape and voltage for applying to the heart. The capacitors should be fully charged before the defibrillation pulse is generated. The power supply of the ICD is typically a battery generating a voltage of only about 3.3 volts. Hence, one or more flyback transformer are provided between the power supply and the pair of defibrillation capacitors to incrementally charge the defibrillation capacitors prior to delivery of a defibrillation pulse. In many ICDs, the pulse delivery circuit includes a set of four insulated gate bipolar transistors (IGBTs) formed in an H-bridge configuration. The IGBTs are switched on and off so as to apply charge stored in the capacitors in biphasic pulse waveform to the heart. To switch an IGBT on, a voltage of about 15 volts usually needs to be applied to a gate of the IGBT. Hence, a pair of non-flyback transformers are provided for converting the voltage provided by the power supply to the voltage required to switch on the IGBTs of the pulse delivery circuit.

In any implantable cardiac stimulation device, particularly, ICDs, it is critical that the size of the device be minimized and that reliability be maximized. Size must be minimized to make the device as small and light as possible to reduce discomfort to the patient after the device has been implanted. Reliability must be maximized to ensure that the patient receives the appropriate therapy at all times and that the device need not be explanted from the patient to replace malfunctioning components. As can be appreciated, if an ICD fails to deliver adequate defibrillation therapy, the patient may not survive an episode of ventricular fibrillation. Unfortunately, conventional techniques for implementing transformers with ICDs neither minimize device size or maximize device reliability.

In particular, the flyback and non-flyback transformers for use in ICDs are typically configured using transformer coils and core members which are physically separate from one another and from other electrical components of the device, such as from printed circuit boards (PCBs) containing capacitors, switching transistors and the like. The transformer coils and core members consume considerable volume individually and, since they are separate from other components, additional space is needed to accommodate the necessary electrical interconnections. Hence, size is not minimized. Moreover, with transformer coils and core members installed separately from other components, reliability is not optimal as electrical interconnection problems could arise during fabrication or during operation of the device. In particular, given the high voltage generated by the flyback transformers, heat generated by electrical resistance could possibly damage electrical interconnections between the flyback transformer coil and other components of the device causing the device to fail.

Thus, it would be highly desirable to provide improved transformer assemblies for use within ICDs or other implantable cardiac stimulation devices which addresses the aforementioned concerns and it is to that end that aspects of the invention are primarily directed.

SUMMARY OF THE INVENTION

In accordance with the invention, an improved transformer assembly is provided for use in an ICD or other implantable cardiac stimulation device. The transformer assembly is coupled between a power supply and a pulse delivery circuit for transforming the voltage of the power supply to voltages required by the pulse delivery circuit. The power transformer assembly is formed using a PCB having transformer coil windings or turns embedded therein with one or more transformer cores mounted adjacent to the windings of the PCB.

In an exemplary embodiment, the transformer cores are generally planar ferrite cores with a set of feet for mounting into a set of apertures formed in a multi-layer PCB. The coils of the transformers are embedded within the layers of the PCB with one or more coil turns or loops per layer. Other circuit components such as capacitors, transistors and the like may also be mounted to or embedded in the PCB. By embedding the coil windings of the transformers within the PCB, the transformers may be more easily integrated with other circuit components so that the overall size of the stimulation device may be reduced. Moreover, the use of a PCB helps avoid reliability problems that might otherwise occur in the fabrication, assembly and operation of the device. For example, a switching transistor for controlling the operation of a transformer can be mounted to the same PCB as the transformer coil thereby eliminating the need for potentially bulky device interconnection lines between the switching transistor and the transformer coil thereby reducing size and improving reliability.

In a specific exemplary embodiment, a primary and two secondary transformers are provided for use with a twelve-layer PCB. The primary transformer is used as a flyback transformer for charging a pair of defibrillation capacitors. The two secondary transformers are used to provide voltage for selectively switching on a set of four IGBTs formed in an H-bridge configuration so as to apply charge stored in the capacitors in biphasic pulse waveform to the heart. The coil of the flyback transformer is embedded within the four middle layers of the twelve-layer PCB within one turn per layer. The coils of the two secondary transformers are embedded within the top four and bottom four layers, respectively, of the PCB, with three turns per layer.

In another specific exemplary embodiment, wherein a primary and two secondary transformers are also provided, only the coil of the primary transformer is embedded within the PCB. The coils of the two secondary transformers are affixed to the surface of the PCB. As with the preceding embodiment, the primary transformer is used as a flyback transformer and the two secondary transformers are used to provide voltage to H-bridge switching IGBTs for applying biphasic pulse waveforms to the heart.

Numerous other embodiments are consistent with the invention as well. Other embodiments, advantage and features of the invention are discussed below.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
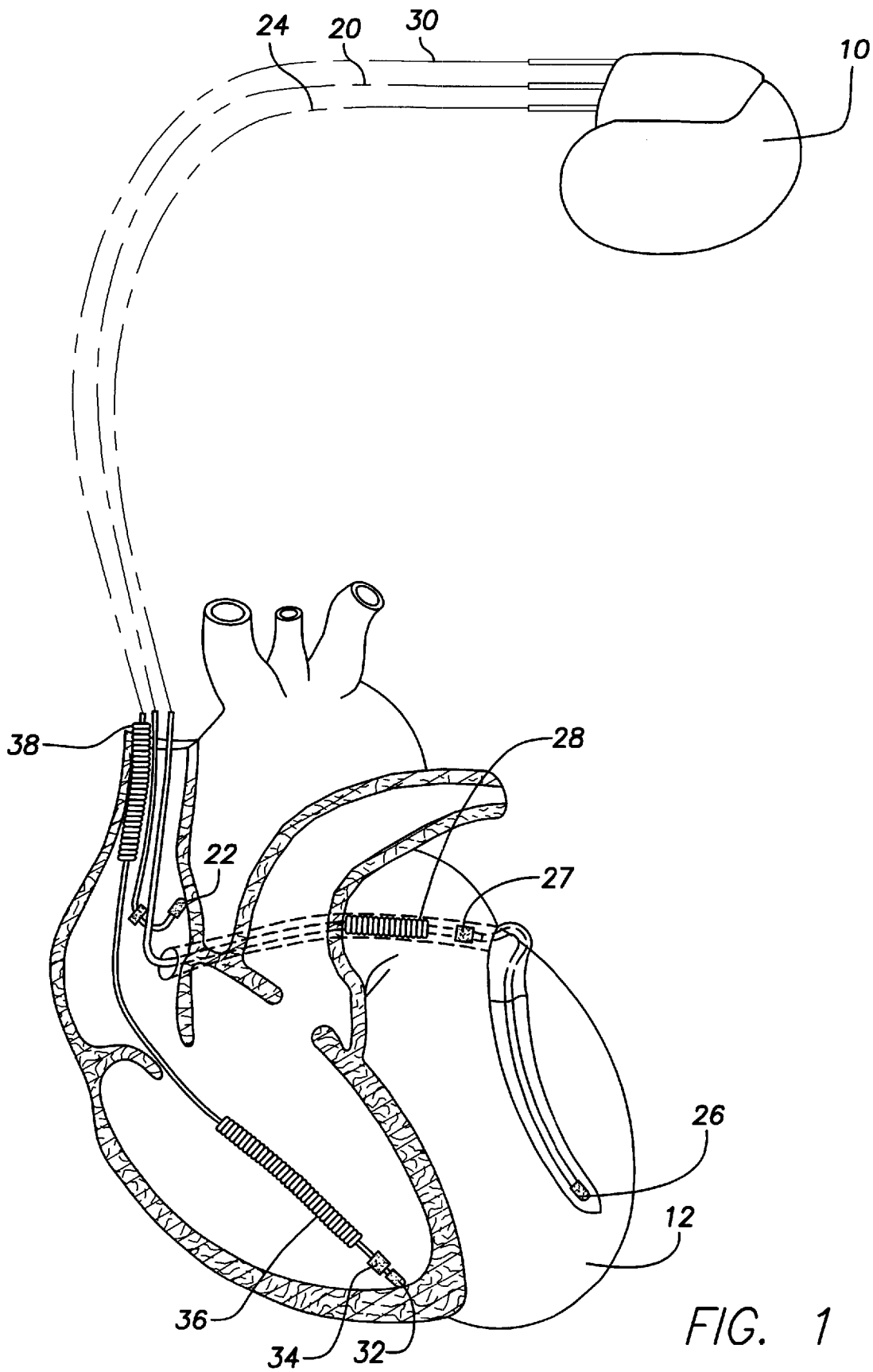
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999 entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
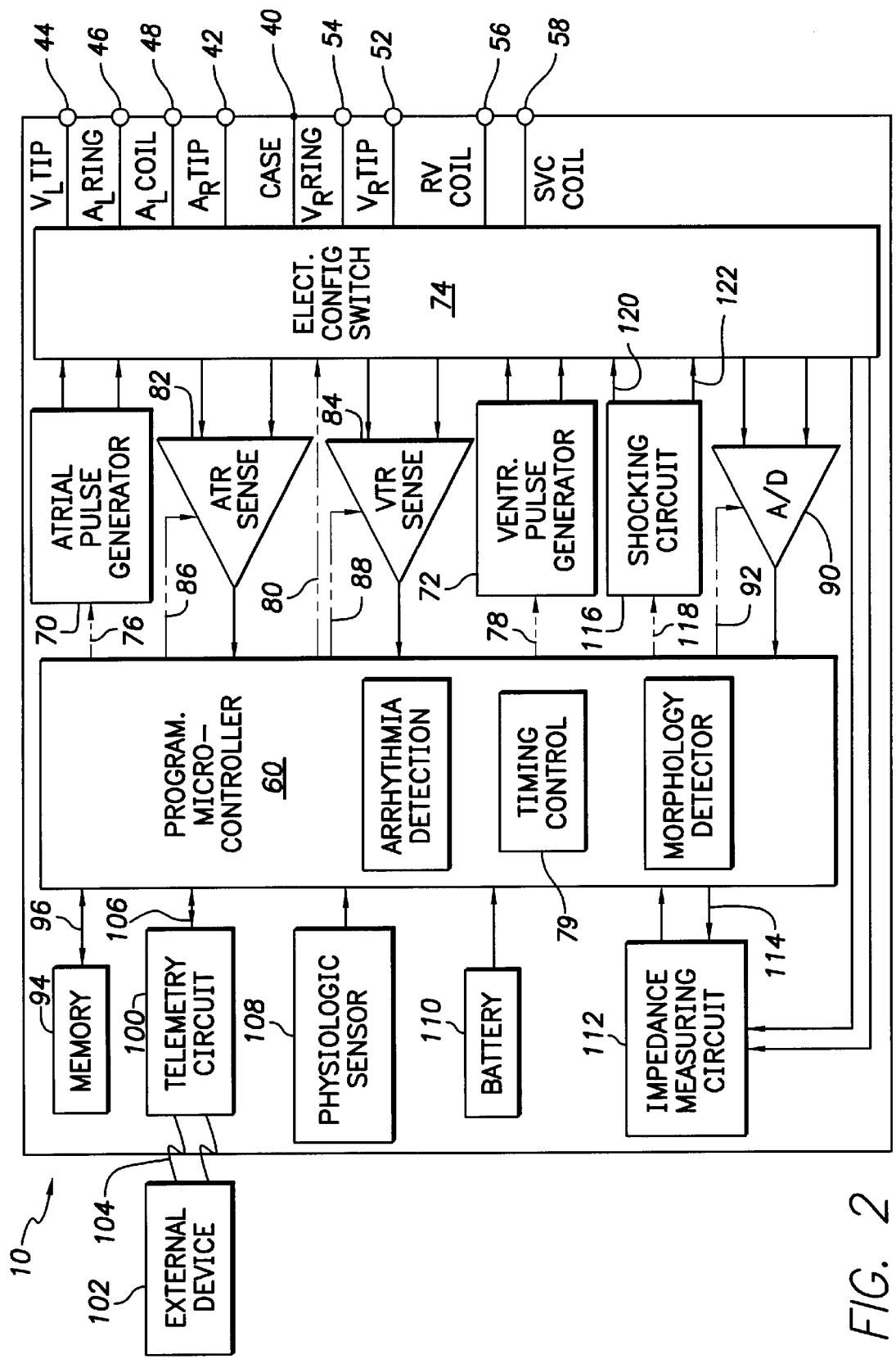
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Shocking circuit 116 includes a transformer assembly for transforming a voltage received from battery 110 to voltages appropriate for charging capacitors of the shocking circuit. A shocking pulse is output from the shocking circuit along lines 120 and 122 to switch 74 for routing to the appropriate leads. The transformer assembly of the shocking circuit is configured so as to reduce overall space and maximize reliability. The transformer assembly and the overall shocking circuit in which it is contained will now be described in greater detail with reference to the remaining figures.

Figure 3:
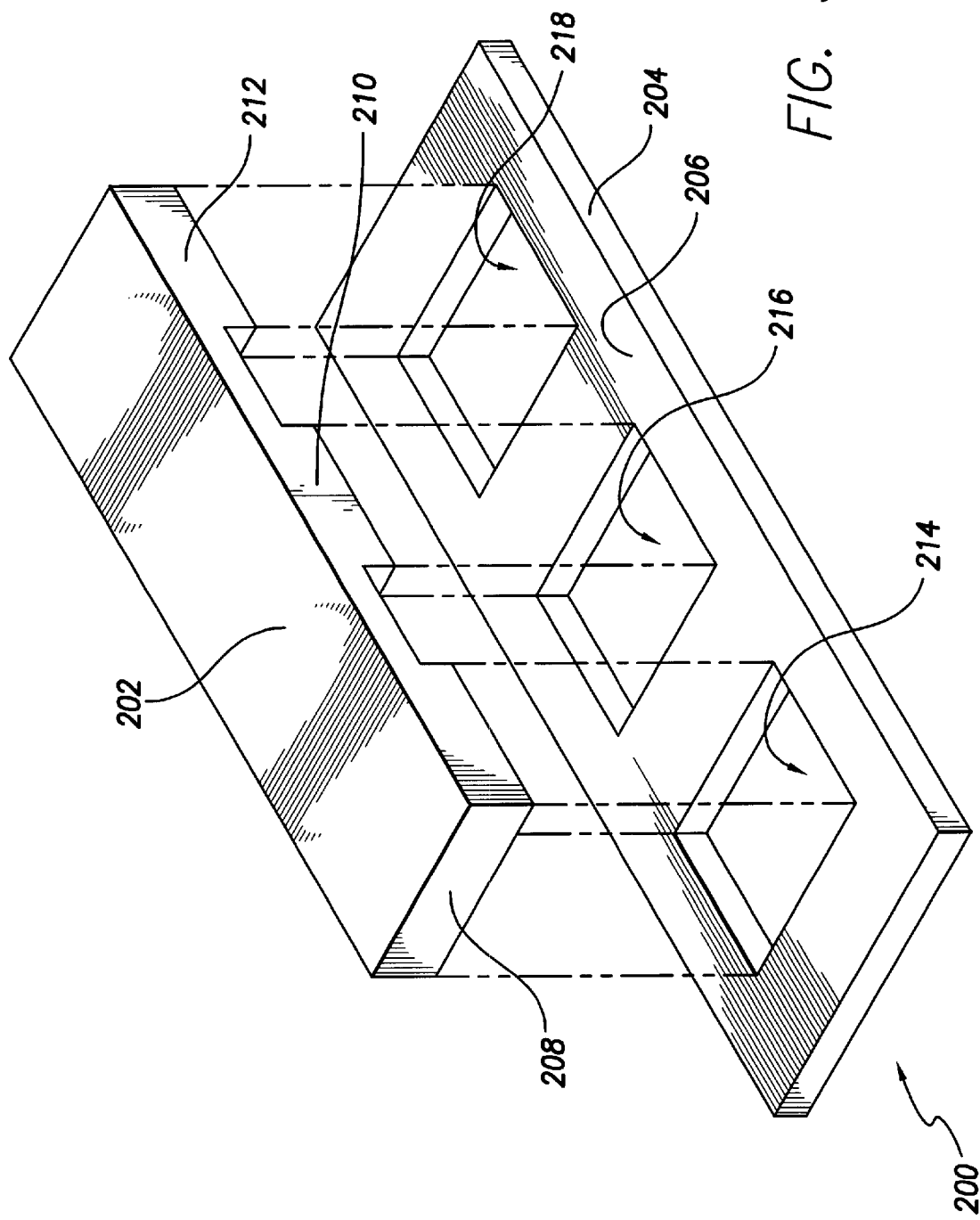
FIG. 3 is an exploded perspective view of a transformer assembly for use within a shocking circuit of the stimulation device of FIG. 2 wherein the transformer assembly is formed using a PCB in accordance with an exemplary embodiment of the invention.

FIG. 3 illustrates a transformer assembly 200 for use within shocking circuit 116 (FIG. 2) for converting a voltage generated by battery 110 (also FIG. 2) for charging capacitors within the shocking circuit to permit delivery of a defibrillation pulse. The transformer assembly includes a generally planar ferrite core 202 and a PCB 204 having a transformer coil 206 embedded therein. The coil, which is embedded in the PCB, is shown in phantom lines and is represented in FIG. 3 by only a single coil turn. The coil actually may have one or more turns per layer. Interconnection lines connecting ends of the coil to input/output lines are not shown. The PCB may have additional circuit components such as transistors and capacitors as well. In a preferred implementation discussed below, a set of three planar cores are provided and the PCB has three corresponding sets of coils embedded therein, to accommodate a primary and two secondary transformers with the single PCB. Within FIG. 3, only a single transformer core and a single corresponding transformer coil are illustrated so that the pertinent structural features of a single transformer are more easily viewed.

Planar core 202 includes has a set of three downwardly-extending feet or projections 208, 210 and 212 received in corresponding windows or apertures 214,216 and 218 of the PCB. Coil 206 encircles central window 216 between central window 216 and the outer pair of windows 214 and 218. Hence, coil 206 likewise encircles central foot 210 of the transformer core permitting the coil to generate an output voltage differing from an in voltage applied to the core proportional to the number of turns in the coil. Preferably, the core is glued into place on the PCB with the feet mounted in the windows. Care is taken to ensure that the coil of the PCB is not in direct electrical contact with the core. This may be achieved by embedding the coil within interior layers of the PCB. Preferably, the coil is embedded in the PCP so as to provide one or more turns or loops of the coil within each of several layers of the PCB to accommodate the total number of loops needed to achieve the desired voltage transformation. In one example, wherein the transformer is used as a flyback transformer, the coil is formed within four layers of the PCB with one loop per layer thereby providing a coil with four total turns.

Figure 4:
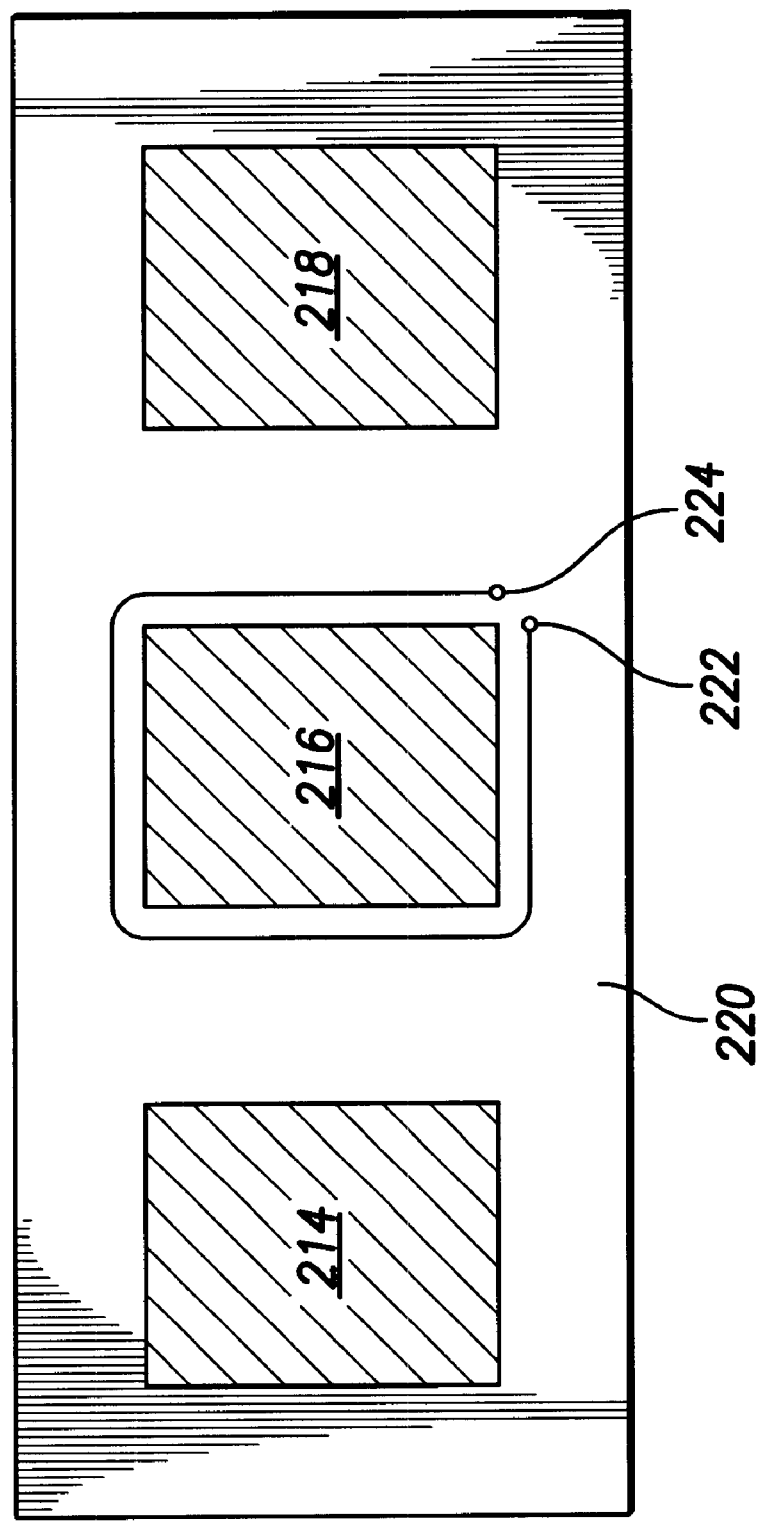
FIG. 4 is a cross-sectional schematic representation of the transformer assembly of FIG. 3 particularly illustrating one layer of the PCB of the assembly.

FIG. 4 illustrates one horizontal layer 220 of the PCB illustrating one loop of a single layer of the coil. Opposing ends 222 and 224 of the coil layer are connected to the next higher and next lower layers, respectively, via vertical connection lines (not shown). For a coil layer embedded within layer #3 of the PCB, the opposing ends are thereby connected to layers #2 and #4, respectively. Other intermediate layers of the PCB are configured identically to that of the layer of FIG. 4. Top and bottom players of the PCB are likewise configured identically, but with the exception that, for the top layer, an outer end of the coil is connected to an input voltage terminal and, for the bottom layer, an inner end of the coil is connected to an output voltage terminal.

Figure 5:
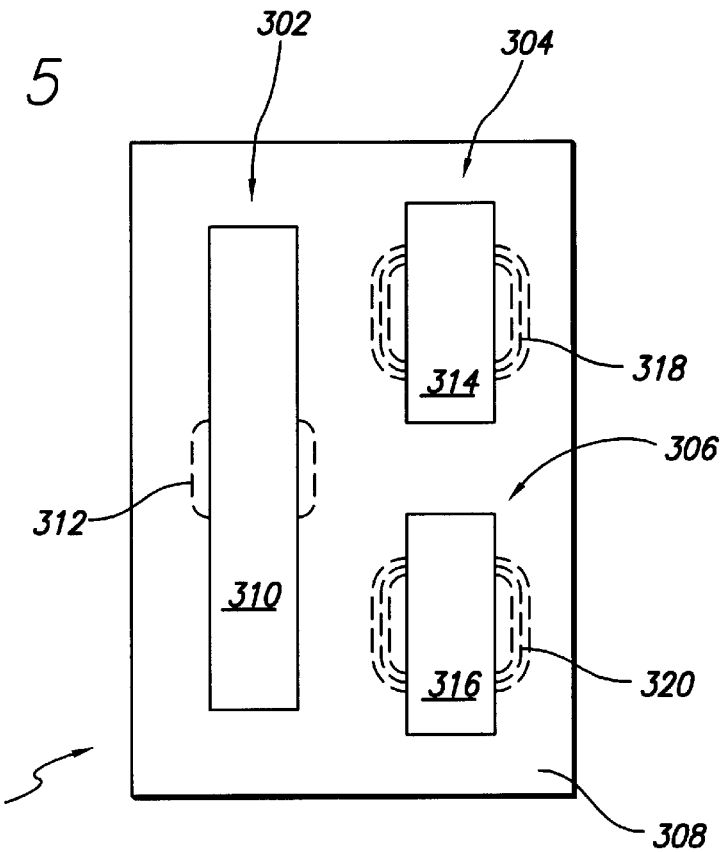
FIG. 5 is a top planar view of a specific exemplary embodiment of the transformer assembly for use within the shocking circuit of FIG. 2 wherein the transformer assembly has a primary and two secondary transformers each of which has windings embedded within a PCB.

In a preferred implementation, the transformer assembly includes a primary transformer and a pair of secondary transformers. FIG. 5 illustrates an example wherein a transformer assembly 300 has a primary transformer 302 and a pair of secondary transformers 304 and 306. The assembly includes a twelve-layer PCB 308. Primary transformer 302 has a generally planar ferrite core 310 and a set of coil windings 312 embedded within the PCB. Secondary transformers 304 and 306 each include a smaller planar ferrite core 314 and 316, respectively, and sets of coil windings 318 and 320, respectively, also embedded within the PCB. In FIG. 5, the coils embedded in the PCB are shown in phantom lines. Interconnection lines to input/output pads are not separately shown.

The coils of the primary and two secondary transformers are embedded within separate layers of the PCB. The coils for secondary transformer 304 are embedded in top layers #1–#4; the coils for primary transformer 302 are embedded within middle layers #5–#8; and the coils for secondary transformer 306 are embedded within bottom layers #9–#12. As shown in FIG. 5, coils of the separate transformers may be spaced horizontally apart from one another. Alternatively, the coils may cover a greater portion of the PCB and thereby overlap one another. Since the overlapping coils are embedded on different layers of the PCB, overlapping coils do not physically interfere with one another. In either case, providing coils on separate layers of the PCB helps reduces the total surface area required for the PCB and hence can reduce the overall size of the implantable device.

The coil of the primary transformer has one turn per layer thereby providing a coil with four total turns. The coils of the secondary transformers are formed with three turns per layer thereby providing coils with twelve total turns. The primary transformer is preferably employed as a flyback transformer for incrementally converting a voltage of about 3.3 volts to about 1500 volts for incrementally charging a pair of defibrillation capacitors. The secondary transformers are preferably employed as a conventional transformers for converting a voltage of about 3.3 volts to about 15 volts for applying to the gates of IGBT switching transistors. Even though the total voltage conversion for the flyback transformer is great, relatively few coil turns are required because the flyback transformer only converts the voltage incrementally. Even though the total voltage conversion for the secondary transformer is much smaller, more coil turns are required because the secondary transformers must convert the voltage substantially immediately.

Figure 6:
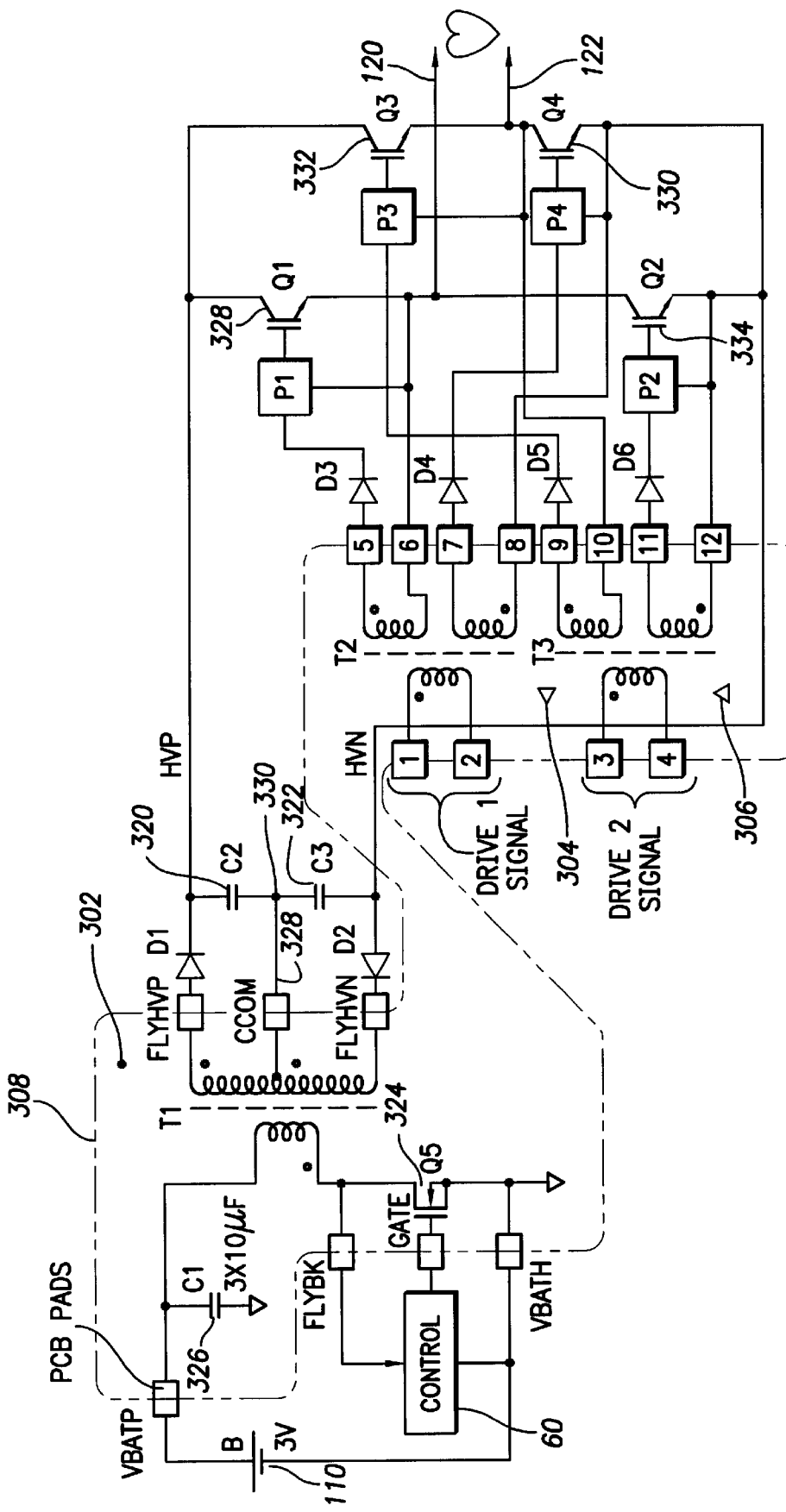
FIG. 6 is a schematic of a circuit employing the transformer assembly of FIG. 5.

FIG. 6 is a schematic of a circuit incorporating the transformer assembly of FIG. 5. Primary transformer 302 is connected between battery 110 and a pair of pulse delivery capacitors 320 and 322 for use as a flyback transformer. Flyback transformer 302 converts a voltage generated by battery 110 (typically 33 volts) to a voltage appropriate for charging the pair of high voltage capacitors (typically 1500 volts) to permit delivery of a high voltage defibrillation pulse. The output of the defibrillation pulse is controlled by a set of four IGBTs (328, 330, 332, and 324) arranged in an H-bridge configuration. The IGBTs are selectively triggered by drive signals applied to their gates via secondary transformers 304 and 306 to provide a biphasic defibrillation pulse. The biphasic pulse is output on lines 120 and 122 to switch 74 (FIG. 2) where it is routed to the appropriate shocking leads.

Briefly, the circuit operates as follows. Controller 60 applies a high frequency gating signal to a flyback control transistor 324 to cause charge to be quickly and incrementally stored within capacitors 320 and 322 at a combined voltage of about 1500 volts. Two capacitors are provided because single capacitors capable of accommodating 1500 volts are not typically practicable. To discharge the defibrillation pulse, a first drive signal at the battery voltage is applied to transformer 304 and converted to a voltage sufficient for triggering IGBTs 328 and 330 (typically 15 volts). The converted drive signal is applied to the gates of IGBTs 328 and 330 causing the high voltage capacitors to begin to discharge. As a result, a positive voltage pulse is applied to the heart via output lines 120 and 122. Then, the first drive signal applied to transformer 304 is switched off and a second drive signal is applied to transformer 306. Transformer 306 converts the voltage of the second drive signal to a voltage sufficient to trigger IGBTs 332 and 334 (also typically 15 volts) causing the high voltage capacitors to continue discharging, this time through IGBTs 332 and 334. Hence, the polarization of the defibrillation pulse is switched from positive to negative, thus providing the biphasic pulse waveform. Eventually, the charge in the high voltage capacitors is discharged, and the second drive signal is deactivated. If a second defibrillation pulse is required, the high voltage capacitors are again charged using the flyback transformer and the sequence of first and second drive signals are again applied to the secondary transforms. Although, not shown in the circuit schematic, the drive signals applied to the secondary transformers are provided by controller 60.

In FIG. 6, circuit components of transformer assembly PCB 308 are encircled in phantom lines. As noted above, the coils for the primary flyback transformer and the pair of secondary transformers are all embedded within the PCB. Flyback transistor 324 is also formed on the PCB as well as a small flyback circuit capacitor 326. Note that, to permit single flyback transformer 302 to charge both defibrillation capacitors 320 and 322, an interconnection line 328 is provided between the coil of the flyback transformer and a node 330 between the two defibrillation capacitors. Input/output connection pads for the PCB are shown in the figure. The various other components of the overall circuit shown in the figure are provided on other PCBs mounted separately within the medical device.

Figure 7:
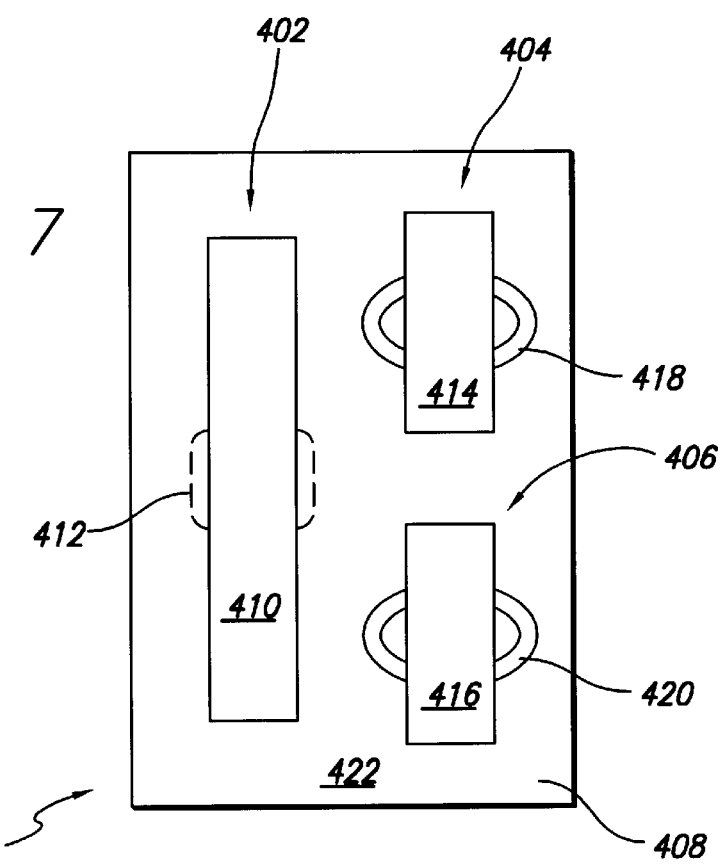
FIG. 7 is top planar view of another specific exemplary embodiment of the transformer assembly for use within the shocking circuit of FIG. 2 wherein the transformer assembly also has a primary and two secondary transformers but wherein only the windings of the primary transformer are embedded within the PCB.

FIG. 7 illustrates an alternative implementation of wherein only the coils of the primary flyback transformer are embedded within the PCB. The coils of the secondary transformers are instead mounted between the cores of the secondary transformers and the top surface of the PCB. Briefly, FIG. 7 illustrates a transformer assembly 400 having a primary transformer 402 and a pair of secondary transformers 404 and 406 mounted to a four-layer PCB 408 (internal layers of the PCB are not shown). Primary transformer 402 has a generally planar ferrite core 410 and a set of coil windings (shown in phantom lines) 412 embedded within the four layers of the PCB, with one turn per layer. Secondary transformers 404 and 406 each include smaller planar ferrite cores 414 and 416, respectively, with sets of coil windings 418 and 420, respectively, mounted between the cores and a top surface 422 of the PCB. The coil windings of the secondary transformers are enclosed in an insulating casing so as not to be in direct contact with the cores of the transformers. An advantage of the arrangement of FIG. 7 is that the PCB need not have as many layers or as many internal windings as with the previous embodiment.

What have been described are various embodiments of transformer assemblies for use in an ICD wherein coils of one or more transformers are embedded within a PCB and wherein the cores of the transformers are mounted to the PCB. As noted, by embedding the coil windings of the transformers within the PCB, the transformers may be more easily integrated with other circuit components so that the overall size of the ICD may be reduced. Moreover, the use of a PCB helps avoid reliability problems that might otherwise occur during fabrication, assembly and operation of the device as compared with ICDs having transformers implemented as entirely separate devices that must be separately mounted within the ICD and must be electrically coupled to other components via separate interconnection lines.

Although described primarily with reference to an example wherein the implanted medical device is an ICD, principles of the invention are applicable to other implanted medical devices as well. The exemplary embodiments of the invention described herein are merely illustrative of the invention and should not be construed as limiting the scope of the invention.

What is claimed is:

1. An implantable cardiac stimulation device for delivering electrical pulses to heart tissue comprising:
   a power supply;
   a pulse delivery circuit; and
   a transformer assembly for transforming a voltage of the power supply to a voltage of the pulse delivery circuit, the transformer assembly including a printed circuit board (PCB) having a set of transformer coil windings embedded therein and a transformer core mounted adjacent to the coil windings of the PCB.

2. The device of claim 1 wherein the pulse delivery circuit includes at least one defibrillation capacitor and wherein the transformer is configured as a flyback transformer for use in charging the defibrillation capacitor.

3. The device of claim 1 wherein the core is a planar ferrite core.

4. The device of claim 3 wherein the planar core has a set of projections and the PCB has an equal set of windows, with the projections of the core mounted within corresponding windows of the PCB.

5. The device of claim 4 wherein the planar core has three of the projections, the PCB has an equal set of three windows, and wherein coils of the PCB surround a central window of the PCB and extend between the central window and the other two windows of the PCB, such that the coils surround a central projection of the planar core and between the central projection and the other two projections of the core.

6. The device of claim 1 wherein a plurality of transformers are provided in the transformer assembly, each having a separate core and a separate coil with each of the coils embedded within a single PCB.

7. The device of claim 6 wherein the plurality of transformers includes one primary transformer and two secondary transformers.

8. The device of claim 7:
   wherein the pulse delivery circuit includes a pair of defibrillation capacitors and a set of switching transistors coupled to the pair of defibrillation capacitors; and
   wherein the primary transformer is configured as a flyback transformer for use in charging the defibrillation capacitors and wherein the secondary transformers are coupled to the switching transistors for use in applying switching signals to gates of the transistors.

9. The device of claim 8:
   wherein the switching transistors include a set of four insulated gate bipolar transistors (IGBTS) connected in an H-bridge configuration; and
   wherein the two secondary transformers provide voltages for selectively switching on the set of four IGBTs so as to discharge charge stored in the defibrillation capacitors in biphasic pulse waveform.

10. The device of claim 6 wherein the PCB includes a plurality of layers and wherein coils of the primary transformer and of the secondary transformers are embedded within different layers of the PCB.

11. The device of claim 6:
    wherein a plurality of transformers are provided in the transformer assembly, each having a separate core and a separate coil and
    wherein the coil of the primary transformer is embedded in the PCB and wherein the coils of the secondary transformers are mounted externally to the PCB.

12. An implantable cardiac stimulation device for delivering defibrillation pulses to heart tissue comprising:
    means for detecting fibrillation in the heart tissue;
    means for storing a defibrillation charge;
    means for charging the means for storing the defibrillation charge with an amount of charge appropriate for use as a defibrillation pulse;
    means for delivering the defibrillation pulse to the heart tissue by selectively discharging charge stored in the means for storing the defibrillation charge; and wherein
    the means for charging includes a transformer assembly having a printed circuit board (PCB) with a set of transformer coil windings embedded in the PCB and a transformer core mounted adjacent to the coil windings of the PCB.

13. The device of claim 12 wherein the means for storing a defibrillation charge includes at least one defibrillation capacitor and wherein the means for charging includes a flyback transformer for use in charging the defibrillation capacitor.

14. The device of claim 12:
    wherein the means for delivering the defibrillation pulse to the heart tissue includes a set of switching transistors and a pair of secondary transformers for applying switching signals to gates of the transistors and
    wherein coils of the secondary transformers are also embedded in the PCB and wherein transformer cores of the secondary transformers are also mounted adjacent to the PCB.

* * * * *